(12) United States Patent
Günther et al.

(10) Patent No.: US 11,629,374 B2
(45) Date of Patent: Apr. 18, 2023

(54) DETECTION METHOD AND DEVICE

(71) Applicants: Rolf Günther, Hamburg (DE); Tobias Pöhlmann, Zwickau (DE); Heinrich Maria Schulte, Hamburg (DE)

(72) Inventors: Rolf Günther, Hamburg (DE); Tobias Pöhlmann, Zwickau (DE); Heinrich Maria Schulte, Hamburg (DE)

( * ) Notice: Subject to any disclaimer, the term of this patent is extended or adjusted under 35 U.S.C. 154(b) by 116 days.

(21) Appl. No.: 16/592,992

(22) Filed: Oct. 4, 2019

(65) Prior Publication Data
US 2020/0032318 A1 Jan. 30, 2020

Related U.S. Application Data

(63) Continuation-in-part of application No. PCT/EP2018/000144, filed on Apr. 4, 2018.

(30) Foreign Application Priority Data

Apr. 5, 2017 (DE) .................. 10 2017 003 312.9

(51) Int. Cl.
*C12Q 1/686* (2018.01)
*G01N 33/543* (2006.01)

(52) U.S. Cl.
CPC ....... *C12Q 1/686* (2013.01); *G01N 33/54306* (2013.01)

(58) Field of Classification Search
CPC .............. C07K 16/2896; C12Q 1/6844; C12Q 2537/143; C12Q 2563/159; C12Q 1/686; C12Q 1/689
See application file for complete search history.

(56) References Cited

U.S. PATENT DOCUMENTS

| 2003/0036086 A1 | 2/2003 | Leonard et al. |
| 2011/0195437 A1* | 8/2011 | Brozek .............. G01N 33/5055 435/7.92 |

FOREIGN PATENT DOCUMENTS

| WO | 1994/029728 A1 | 12/1994 |
| WO | 2010/015633 A1 | 2/2010 |
| WO | 2013/091102 A1 | 6/2013 |
| WO | 2015/200788 A1 | 12/2015 |
| WO | 2018/184719 | 11/2018 |

OTHER PUBLICATIONS

Cecrdlova et al., "Manumycin A downregulates release of proinflammatory cytokines from TNF alpha stimulated human monocytes," Immunology Letters, published on-line November, vol. 169, pp. 8-14. (Year: 2015).*
Moller et al., "Chemokine production and pattern recognition receptor (PRR) expression in whole blood stimulated with pathogen-associated molecular patterns (PAMPs)," Cytokine, vol. 32, pp. 304-315. (Year: 2005).*
Cesar et al., "Expression Patterns of Ubiquitin, Heat Shock Protein 70, alpha-Actin, and beta-Actin Over the Molt Cycle in the Abdominal Muscle of Marine Shrimp Litopenaeus Vannamei," Molecular Reproduction and Development, vol. 74, pp. 554-559. (Year: 2007).*
Gibellini et al., "Simultaneous detection of HCV and HIV-1 by SYBR Green real time multiplex RT-PCR technique in plasma samples," Molecular and Cellular Probes, vol. 20, pp. 223-229. (Year: 2006).*
English translation of the International Search Report (ISR) for PCT/EP2018/000144 dated May 23, 2018, pp. 1-4.
Loonen, Anne J.M. et al. "Comparison of Pathogen DNA Isolation Methods from Large Volumes of Whole Blood to Improve Molecular Diagnosis of Bloodstream Infections" PLOS ONE (2013) vol. 8(8), p. e72349.
Afshari, Arash et al. "Bench-to-bedside review: Rapid molecular diagnostics for bloodstream infection—a new frontier?" Critical Care (2012) vol. 16(3) pp. 1-12.
Hardingham, Jennifer E. et al. "Immunobead-PCR: A Technique for the Detection of Circulating Tumor Cells Using Immunomagnetic Beads and the Polymerase Chain Reaction" Cancer Research (1993) vol. 53, pp. 3455-3458.
Banada, Padmapriya P. et al. "Highly Sensitive Detection of *Staphylococcus aureus* Directly from Patient Blood" PLOS ONE (2012) vol. 7(2), p. e31126.
Noisakran, Sansanee et al. "Detection of Dengue Virus in Platelets Isolated from Dengue Patients" Southeast Asian Journal of Tropical Medicine and Public Health (2009) vol. 40(2), pp. 253-262.
Ariede, Jovita Ramos et al. "Platelets can be a biological compartment for the Hepatitis C Virus" Brazilian Journal of Microbiology (2015) vol. 46(2), pp. 627-629.
Youssefian, Tayebeh et al. "Host defense role of platelets: engulfment of HIV and *Staphylococcus aureus* occurs in a specific subcellular compartment and is enhanced by platelet activation" Blood (2002) vol. 99(11), pp. 4021-4029.
Schmidt, Tina et al. "Detection of Antigen-Specific T Cells Based on Intracellular Cytokine Staining Using Flow-Cytometry" Molecular Typing of Blood Cell Antigens In: Methods in Molecular Biology (2013) vol. 1064, pp. 267-274.

* cited by examiner

*Primary Examiner* — Young J Kim
(74) *Attorney, Agent, or Firm* — McDonnell Boehnen Hulbert & Berghoff, LLP

(57) ABSTRACT

The disclosure concerns a method and a device for enriching cells, cell fragments and molecules from whole blood for a specific detection of at least one population of cells, cell fragments or molecules contained therein. The task was to detect a broad spectrum of target objects including their molecules simply, quickly and yet sensitively and specifically from whole blood. According to the disclosure, not the target objects themselves, but matrix objects are specifically enriched, but target objects are specifically analyzed and thus a specific and sensitive detection of target objects is achieved.

4 Claims, 3 Drawing Sheets

Fig. 3

| | |
|---|---|
| | 1. Collection of the blood sample, buffer |
| Processes which are Performed in the cartridge | 2. Addition of reagents for the enrichment |
| | 3. Enriching the matrix objects using beads |
| | 4. Wash processes |
| | 5. Distribution of the enriched matrix objects in several sample carriers |
| | 6. Addition of reagents for the qPCR |
| | 7. Performing the qPCR |
| | 8. Quantification of the target objects |
| | 9. Analysis |

DETECTION METHOD AND DEVICE

CROSS REFERENCE

This application is a continuation in part of PCT/EP2018/000144 filed Apr. 4, 2018, which claims priority to German application DE 102017003312.9 filed Apr. 5, 2017.

BACKGROUND

Especially at low concentrations (especially smaller than 1000 cells per ml whole blood) of the target objects to be analyzed in whole blood, a limitation of the detection limit (especially the sensitivity and specificity) of the detection methods becomes apparent.

For this reason, established methods aim to prepare the sample material as completely as possible in order to provide as much analyte as possible for the detection procedure (Banada et al. 2012).

In addition, technologies have been developed that can be used to specifically enrich the target objects or the whole blood molecules contained in them. The "Cell Collector" from Gilupi, Potsdam, is a device for enriching circulating tumour cells in vivo on the surface of a metal rod. MagNA Lyser beads from Roche Diagnostics, Mannheim, are ceramic magnetobeads for the mechanical disruption of cells and the subsequent enrichment of the DNA they contain. Similarly, the beads of the µMACS series from Miltenyi, Bergisch-Gladbach are used for the enrichment of DNA and RNA from cells. This procedure may increase the sensitivity and specificity of the detection. However, these procedures are time consuming and they usually require much equipment. In addition, these methods are usually based on individual molecular target structures that are characteristic of the target objects. This means that target objects or their molecules are specifically enriched depending on the capture structures used, for example antibodies. For example, the use of antibodies to enrich a particular pathogen species may not enrich other simultaneously occurring pathogens.

In addition, technologies have been developed to increase specificity by enriching isolated target DNA from the analysed whole blood samples. The VYOO platform of Analytik Jena, Jena, Germany, uses affinity chromatography with an immobilized protein derived from CXXC scavenger protein 1 to specifically enrich the DNA of pathogens (Popp et al., 2015). One disadvantage of this method is the time consuming preparation (hands-on time).

Especially for the detection of pathogens in low concentrations in whole blood, non-molecular, state of the art methods comprise blood culture, in which the pathogens are cultivated for a few hours or even days before detection in order to increase the sensitivity of the detection, are therefore often preferred. This cultivation can also be preceded by molecular detection. In any case, these cultivation methods are time-consuming, labor-intensive, and problematic in that not all pathogens in the blood culture can be cultivated or multiplied and detected equally (Striebel, 2014, Thalhammer et al, 2016). This results in limited sensitivity or specificity.

The disadvantage of all methods in the state of the art is that they are far too slow in practical application. However, in the case of the detection of pathogens in the clinical picture, for example sepsis or endocarditis, rapid analysis is crucial for successful therapy (Afshari et al., 2012). The high equipment and logistics effort, and the complexity of the described methods require that the test can only be reliably carried out by especially qualified employees with laboratory experience and therefore not or not safely at the point-of-care. Instead, the samples are taken to central laboratories where they are analysed. As a consequence, the time from the patient to the addressee of the test results, especially the attending physician, are usually too long, especially outside regular working hours (Afshari et al., 2012).

DESCRIPTION OF THE FIGURES

FIG. 3: Representation of the proposed workflow according to the invention in detail.

DETAILED DESCRIPTION

Figure 1:
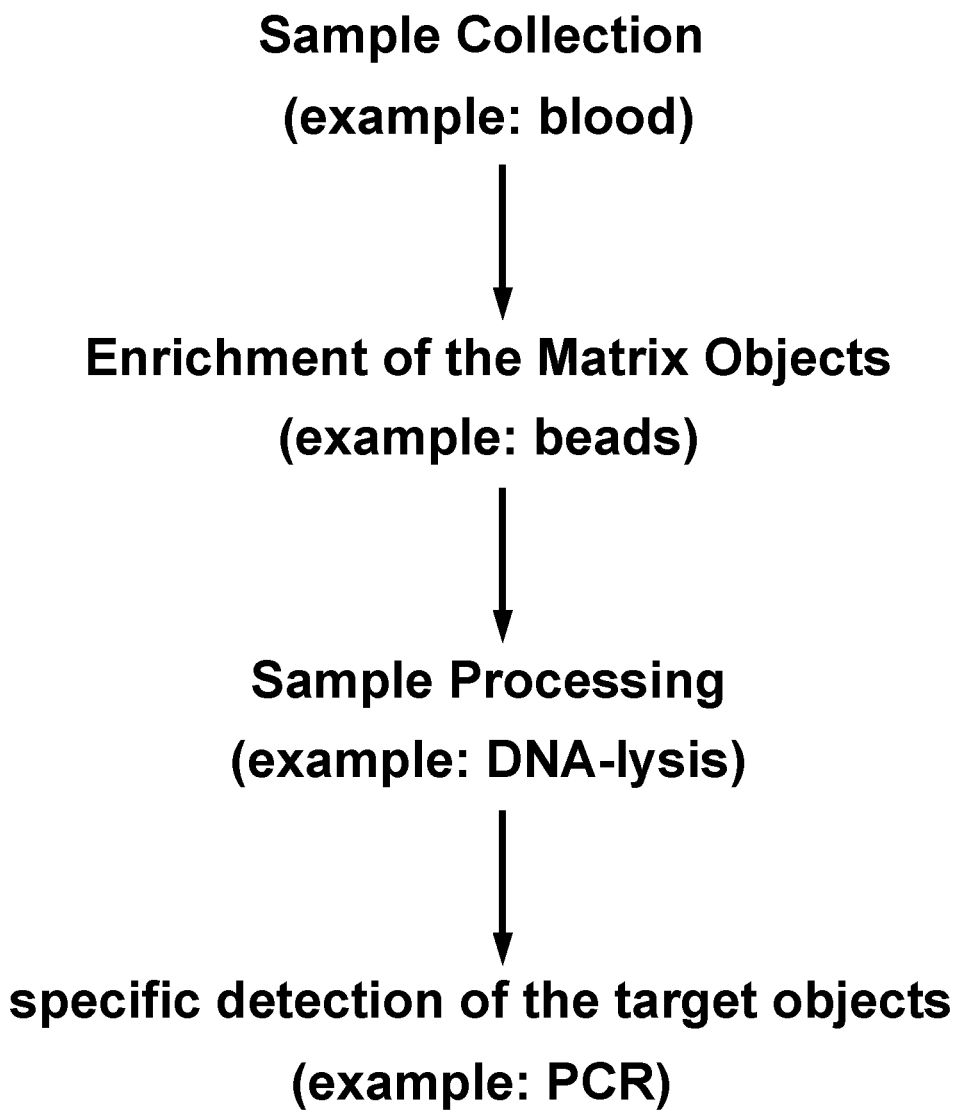
FIG. 1: Representation of the general workflow for the purification of matrix objects and detection of target structures.

The invention concerns a method and a device for enriching cells, cell fragments and molecules from whole blood for a specific detection of at least one population of cells, cell fragments or molecules contained therein.

Cells according to the invention are biological cells, eukaryotic and prokaryotic cells, nucleated or non-nucleated, as well as unicellular organisms, and multicellular organisms. Cell fragments according to the invention are parts of cells, including cell wall components, organelles, membrane components, blood platelets and micelles, as well as viruses. Molecules according to the invention include macromolecules including proteins, peptides, and oligonucleotides such as DNA and RNA, or lipids, carbohydrates, and small molecules.

Cells or viruses to be detected are hereinafter referred to as target objects. Pathogens such as bacteria, fungi, protozoa and viruses may also be target objects. Moreover, fetal cells in the maternal blood or circulating tumour cells may also be targets. The detection method may aim at detecting the DNA, RNA or antigens of the target objects, fragments of the cells, or the whole cells. To simplify matters, these detection methods are also referred to below as detection method of target objects.

Cells that occur jointly with the target cells in whole blood are hereinafter referred to as matrix objects. Matrix cells comprise in particular the various types of immune cells (lymphocytes) as well as erythrocytes and cell fragments such as platelets.

Methods for detecting target objects, their molecules and in particular their DNA from whole blood comprise, for example, molecular biological techniques such as PCR (polymerase chain reaction) or arrays, recently also sequencing, NMR or mass spectroscopy.

The primary object of the current invention is to detect a wide spectrum of target objects including their molecules simply, quickly and yet sensitively and specifically from whole blood.

Surprisingly, it was found that even with incomplete quantitative sample preparation a specific and sensitive detection of target objects can be achieved if only a few populations, especially individual populations of matrix objects of whole blood are enriched prior to sample preparation. This is surprising above all because it is argued in the state of the art that sensitivity and specificity depends primarily on the complete sample processing of the target objects (Banada et al., 2012).

For example, in the case of pathogen infections in whole blood, just a few pathogens (3-1000 pathogens/ml whole blood) can be reliably, specifically and sensitively detected by PCR by enriching matrix objects, in particular immune cells or individual immune cell populations, sample processing, DNA isolation and subsequent PCR. Possibly a specific binding of the matrix objects to target objects such as pathogens or specific phagocytosis processes are associated with this. These effects could increase the ratio of pathogen to eukaryotic material and thus reduce the background signal in some detection methods, especially PCR (Loonen et al, 2013). It is already known that a nested PCR is suitable for the detection of *Staphylococcus aureus* from lymphocytes which are isolated with CD45-labelled magnetic beads and subsequently centrifuged. However, CD45 binds to all lymphocytes and not specifically to individual populations (Banada et al. 2012). Compared to direct PCR from whole blood, however, this method shows no sensitivity advantage and is technically complex due to the use of a centrifuge. The process is also complex and requires many individual steps. The Polaris method (Loonen et al., 2013) also requires centrifugation and several complex single steps.

In the method according to the invention, the matrix objects can be enriched using particles that bind specifically or non-specifically to specific matrix objects. The binding of the particles to the matrix objects can be mediated by coating or coupling the particles with capture molecules, in particular antibodies or other proteins, peptides or aptamers. The particles may have other properties such as magnetic, acoustic or dielectric properties that allow them to be directly enriched or isolated. In another embodiment of the method according to the invention, the size of particles can lie within a specific range so that they can be enriched with a particle filter.

However, the enrichment can also be carried out chromatographically, even if the device requires more complex equipment. In this embodiment, the matrix objects flow past the immobilized beads, especially beads with capture molecules, with which the surface of a flow device is coated. The described beads can also be used as packing material of a chromatographic column. An additional centrifugation step can further improve the enrichment, but increases the complexity of the process. Therefore it can be advantageous to carry out the enrichment without centrifugation step.

The enrichment can also be done with a flow cytometer.

It may be preferable to remove the target objects from the matrix objects before detection.

Matrix objects that can be enriched according to the invention include leukocytes, in particular monocytes, macrophages, B cells, T cells, NK cells, eosinophilic, basophilic and neutrophil granulocytes, dendritic cells, but also erythrocytes. Matrix objects can also be natural cell fragments, including platelets, or cell debris caused by mechanical or chemical action or biological processes such as apoptosis. It may be preferable to enrich more than one population of matrix objects, in particular by using particles or beads specific to several matrix objects or different particles specific to one type of matrix object. However, the accumulation of the entire lymphocyte spectrum is apparently unfavourable (Banada et al., 2012).

The enrichment of the immune cells of the example of an embodiment of the invention is advantageous, for example, via antibodies that are bound to a carrier system (especially particles, especially beads, or solid matrices). Similarly advantageous is to perform the enrichment in fluidic or microfluidic systems, in which the immune cells or particles are enriched by forces or energy input, especially by acoustic or dielectrophoretic effects in the liquid flow, or in the flow cytometer.

It may be advantageous to histologically examine the matrix objects together with the target objects and preferably to analyse them by fluorescence in situ hybridisation or antibody staining.

It can also be advantageous to lyse the enriched matrix objects and thus release the nucleic acids, in particular DNA and RNA of the target objects and in particular the pathogens. Various state-of-the-art processes are available for this purpose, including trizollysis, other chemical methods and mechanical digestion. Subsequent precipitation of the DNA or RNA with ethanol and purification via columns are often advantageous.

PCR, isothermal amplification, sequencing or array-based methods are suitable for the detection of DNA or RNA. multiplex and single PCR can be distinguished in PCR, the latter of which is particularly advantageous because it enables a particularly simple procedure. This makes individual PCR particularly suitable for carrying out the procedure at the point of care and detecting specific pathogens and resistance indicators or genes.

The invention also includes a device for isolation, optionally supplemented by the detection of target objects.

In a specific example of an embodiment of the invention, a cartridge system comprises devices for sample introduction, storage locations for different wash buffers, storage locations for a bead-antibody system for binding specific matrix objects, in particular immune cells, as well as a possibility for lysis of isolated matrix objects, and optionally a device for extracting the RNA or DNA. In the cartridge system, the antibody bead system is added to the whole blood, washed with a wash buffer, the antibody bead system with bound matrix objects is isolated via a sieve system or magnetically, mixed with cell lysis buffer and the precipitated DNA removed. In this cartridge system a fast and simple enrichment of the matrix objects as well as lysis and DNA isolation is carried out in an almost closed container, thus reducing the risk of contamination of the sample with foreign DNA.

In a further embodiment, the RNA or DNA remains in the cartridge system and is not removed. Instead, PCR is performed through a window in the cartridge or with integrated heating and detection elements inside the cartridge. It then contains another storage location for the PCR reagents.

In a further specific example of an embodiment of the invention, the isolated DNA is applied directly to a PCR analysis plate, which contains all chemicals for the analysis of various pathogens in a standardised form. This plate can be produced as multiplex PCR or as a set of single PCR performed in parallel.

The isolated DNA from the cartridge can be applied manually and especially with a pipette or directly from the cartridge via a special dosing system.

DNA lysis in the cartridge and subsequent PCR is only one possibility for analysis; further examples for embodiments performing cell analysis include spectroscopic, enzymatic, colorimetric, histological, chemical-analytical (especially MALDI-TOF-MS), electrochemical and other physical methods (especially NMR).

Furthermore, it can be advantageous to carry out the evaluation of the analysis procedure automatically using software and to compare results with a database and to derive recommendations for therapy, especially directly from guidelines or through adaptive or self-learning procedures.

The process according to the invention, the device according to the invention, and the application kit according to the invention can be used for the detection of a variety of diseases and physiological conditions. These include the following examples:

In the case of Systemic Inflammatory Response Syndrome (SIRS), immediate evidence is of interest as to whether the symptoms observed in the patient are caused by sepsis, i.e. pathogens in the blood stream, or by other causes. Pathogenic viruses, bacteria, fungi or parasites can be detected according to the invention. This proof enables the treating physician to initiate a better antibiotic or anti-pathogen therapy with optimal medication.

Endocarditis also requires the rapid detection of pathogens in the blood for a therapeutic decision. In endocarditis in particular, the conditions for blood culture are considered particularly demanding and time-consuming. (Durack et al. 1994). Pathogens that grow particularly slowly in the laboratory but are relevant for about 3% of endocarditis cases are grouped in the HACEK group (*Aggregatibacter aphrophrophilus, Aggregatibacter actinomycetemcomitans, Cardiobacterium hominis, Eikenella corrodens*, and *Kingella kingae*).

In the case of pneumonia, bacteria can be detected in the urine after a few days. State-of-the-art blood cultures are recommended, especially for nocosomial pneumonia and pneumonia caused by air conditioning systems, which is becoming increasingly common. The method according to the invention also offers the advantage of a faster detection of these infections. Zoonoses are infections with a wide range of manifestations, some of which are diagnosed using blood cultures, some of which last 4-6 weeks, for example when brucellosis is suspected. The method according to the invention also offers the advantage of a faster detection of these infections.

Due to its specific enrichment, the ingenious method also has potential applications for viral diseases, especially for detection of HIV in pregnant women, where a reliable diagnosis is particularly important in order to initiate measures to prevent transmission to the child.

The invention-based method can also be used in the quality and follow-up of CAR-T therapies (Chimeric Antigen Receptor T-cell therapies).

In a specific embodiment, the procedure according to the invention comprises the following steps: First, one or more blood samples are taken from the patient, the coagulation of which is avoided in the EDTA/citrate buffer. Beads, for example anti-CD14 beads from pluriSelect, are added to this sample to bind the matrix objects, for example all CD14-bearing cells such as monocytes and macrophages.

The beads are then separated by a sieve, for example with the Cell Strainer from pluriSelect. The sample with the enriched matrix objects is subjected to DNA lysis in a subsequent step (e.g. tricol precipitation). The sample is then distributed to several sample vessels, for example wells of a-microtiter plate suitable for qPCR. These wells already contain reagents for a qPCR, including primers for a known sequence which are different for each well, and which serves to identify a target object or its resistance to therapy via a genetic marker. Subsequently a single qPCR is performed. Quantification of the signal makes it possible to determine which target objects or resistance genes are present in the sample.

The use of conventional PCR with subsequent gel electrophoresis for the detection of PCR fragments can also be advantageous, just like multiplex PCR.

The invention also comprises an application kit for isolation and analysis of cells, cell fragments and molecules, consisting of at least

- at least one cartridge for isolating matrix objects from whole blood, which can optionally be extended by the capability of DNA isolation
- a sample carrier for the detection, in particular a PCR sample carrier and in particular a PCR sample plate, which contains all reagents for the detection and in particular for carrying out a PCR and the detection of target objects, for example pathogens and optionally their resistances
- dilution and reaction buffer
- one or more probes or syringes with cannula and other necessary materials
- a protocol for application.

The invention is explained in more detail below using the example embodiments shown in the drawings:

FIG. 1 shows the process sequence according to the method of invention. Matrix objects associated with target structures are specifically isolated from a sample. After processing the samples, the actual detection method of the target structures is carried out.

Figure 2:
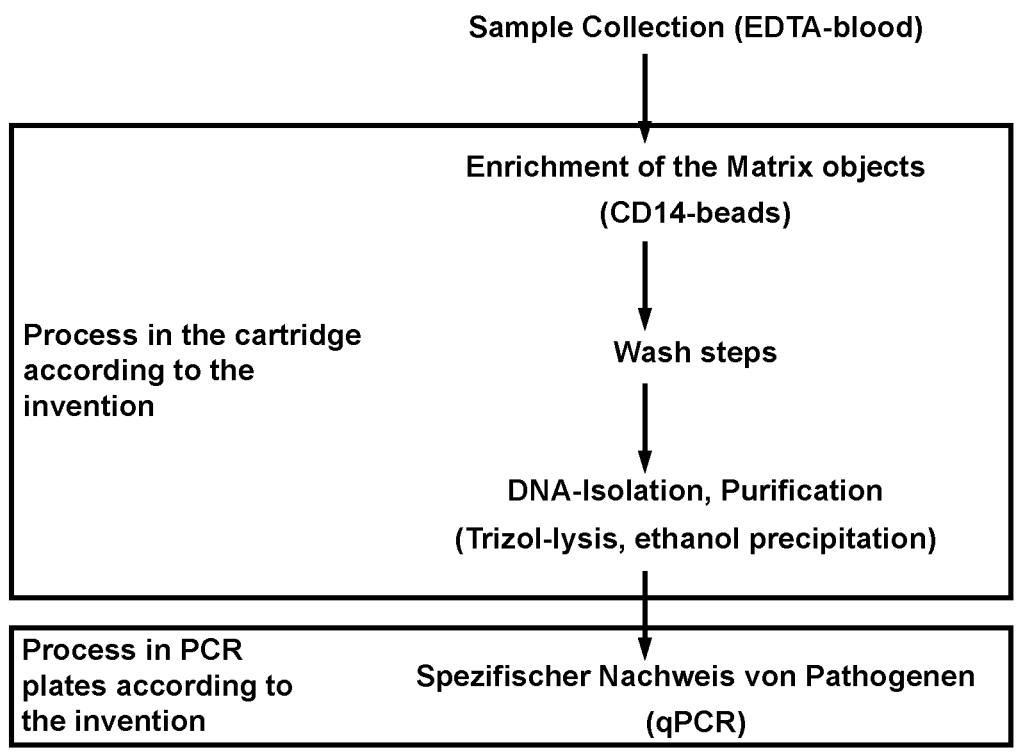
FIG. 2: Representation of the proposed workflow according to the invention, for enrichment of matrix objects and detection of pathogens.

FIG. 2 shows a specific procedure according to the invention for the detection of pathogens in blood. EDTA whole blood is introduced into the cartridge system according to invention, in which the sample is incubated with CD14 beads, washed with buffer and transferred via a sieve system isolating the beads together with trapped monocytes/macrophage (matrix objects) and the pathogens (target objects) contained therein. Cell lysis and isolation/purification of the DNA is then carried out before the DNA sample is transferred with pipettes from the cartridge into the PCR well plates according to the invention. These plates already contain all the chemicals required for PCR in lyophilized form; the polymerase is added to the well plate together with the DNA sample. Subsequently, PCR and thus specific detection of the pathogens is performed. The enrichment of the target objects with the matrix objects or the depletion of non-target objects allows for an increased sensitivity and specificity of the detection method compared to the state of the art; employing the workflow according to the invention and the cartridge system leads to fast results using standard laboratory equipment.

FIG. 3 shows the procedure exemplified in FIG. 2, relating to the detection of pathogens in a blood sample, in more detail. In a first step, a blood sample is collected and diluted with the appropriate buffer solution. In a second step, reagents for enrichment of the matrix objects are added to the sample followed by incubation of the sample with beads leading to the enrichment of said matrix objects (step 3). This step is followed by washing of the sample in step 4. Steps 2 to 4 are performed in the cartridge according to the invention, thereby enabling fast results using standard laboratory equipment. In step 5, enriched matrix objects are distributed to several sample carriers, followed by the addition of reagents for the qPCR (step 6). After qPCR (step 7) and quantification of the target objects (step 8), the results are analyzed, i.e. evaluated (step 9). The final analysis of the target objects performed in the evaluation procedure may be carried out automatically using software enabling, e.g., the comparison of the results obtained with one or more databases. Furthermore, recommendations for therapy may be provided by such software, especially directly from guidelines or through adaptive or self-learning procedures.

LITERATURE

Popp et al. 2015: J. Popp, M. Bauer: "Modern Techniques for Pathogen Detection", John Wiley & Sons, 23 Feb. 2015, p. 86

Streibel 2014: H.-W. Striebel: "Operative Intensivmedizin: Sicherheit in der klinischen Praxis", Schattauer Verlag, 6 Oct. 2014, p. 869

Thalhammer et al. 2016: F. Thalhammer, P. Apfalter, M. Frick, H. Gabriel, R. Gattringer, A. Grisold, R. Krause, Ch. Loewe, L. Müller, H. J. Nesser, A. Wechsler-Fördös, G. Weiss, Ch. Wenisch, S. Winkler, A. Zuckermann, R. Zweiker, K. Huber: "Die infektiöse Endokarditis" Österreichische Ärztezeitung, Supplementum, August 2016, p. 2

Afshari et al., 2012: A. Afshari, J. Schrenzel, M. Ieven, St. Harbarth "Bench-to-bedside review: Rapid molecular diagnostics for bloodstream infection—a new frontier?" Crit Care. 2012; 16(3): 222. Published online 2012 May 29. doi: 10.1186/cc11202

Banada et al. 2012: P. P. Banada, S. Chakravorty, D. Shah, M. Burday, F. M. Mazzella, D. Alland: "Highly Sensitive Detection of *Staphylococcus aureus* Directly from Patient Blood" PLOS one, 17 Feb. 2012 http://dx.doi.org/10.1371/journal.pone.0031126

Loonen et al., 2013: A. J. M. Loonen, M. P. Bos, B. van Meerbergen, S. Neerken, A. Catsburg, I. Dobbelaer, R. Penterman, G. Maertens, P. van de Wiel, P. Savelkoul, A. J. C. van den Brule: "Comparison of Pathogen DNA Isolation Methods from Large Volumes of Whole Blood to Improve Molecular Diagnosis of Bloodstream Infections" August 2013, http://dx.doi.org/10.1371/journal.pone.0072349

Durack et al. 1994: Durack D T, Lukes A S, Bright D K "New criteria for diagnosis of infective endocarditis: utilization of specific echocardiographic findings." Duke Endocarditis Service, Am J Med. 1994 March; 96(3):200-9.

The invention claimed is:

1. A method for the specific detection of target pathogens in whole blood, comprising the steps of:
    (a) collecting a whole blood sample;
    (b) enriching individual, specific blood cell populations selected from the group consisting of monocytes, macrophages, specific leukocyte fractions, erythrocytes, and cell fragments from said whole blood without a centrifugation step and thereby enriching the target pathogens associated therewith together with the enriched blood cell populations, said enriching of said blood cell populations being carried out with the aid of particles, that bind to said specific blood cell populations specifically, said particles having further properties enabling them to be directly enriched or isolated, said further properties being selected from the group consisting of magnetic, acoustic, dielectric properties, and particle size; and
    (c) specifically detecting the target pathogens in the isolated blood cell populations.

2. The method according to claim 1, wherein the step of specifically detecting is performed by at least one single polymerase chain reaction.

3. The method according to claim 1, wherein the step of specifically detecting is performed by a multiplex polymerase chain reaction.

4. The method according to claim 1, wherein the target pathogens are selected from the group consisting of bacteria, viruses, fungi, and protozoa.

\* \* \* \* \*